United States Patent [19]

Oxman et al.

[11] Patent Number: 5,026,278
[45] Date of Patent: Jun. 25, 1991

[54] DENTAL IMPRESSION TRAY WITH FLANGE

[75] Inventors: Joel D. Oxman; F. Andrew Ubel, III, both of St. Paul, Minn.

[73] Assignee: Minnesota Mining and Manufacturing Company, St. Paul, Minn.

[21] Appl. No.: 484,105

[22] Filed: Feb. 23, 1990

[51] Int. Cl.$^5$ ............................................. A61C 9/00
[52] U.S. Cl. .......................................... 433/41; 433/37; 433/48
[58] Field of Search ........................ 433/37, 38, 39, 48, 433/68, 71, 41, 47; 128/831

[56] References Cited

U.S. PATENT DOCUMENTS

| D. 278,274 | 4/1985 | Levine | D24/10 |
|---|---|---|---|
| 1,561,052 | 11/1925 | Brown . | |
| 1,910,740 | 5/1933 | Barsha | 433/38 |
| 1,955,709 | 4/1934 | Kinsley | 32/6 |
| 3,250,004 | 5/1966 | Jones | 433/38 |
| 3,473,225 | 10/1969 | Deuschle et al. | 32/17 |
| 3,505,995 | 4/1970 | Greenberg | 433/37 |
| 3,654,703 | 4/1972 | McAdoo | 32/17 |
| 3,878,610 | 4/1975 | Coscina | 433/37 |
| 4,227,877 | 10/1980 | Tureaud et al. | 433/37 |
| 4,361,528 | 11/1982 | Ginsburg et al. | 264/28 |
| 4,401,616 | 8/1983 | Wagner | 264/138 |
| 4,413,979 | 11/1983 | Ginsburg et al. | 433/41 |
| 4,619,610 | 10/1986 | Pelerin | 433/41 |
| 4,684,343 | 8/1987 | Schreinemakers | 433/214 |
| 4,768,951 | 9/1988 | Abiru et al. | 433/48 |

FOREIGN PATENT DOCUMENTS

| 885772 | 1/1954 | Fed. Rep. of Germany . | |
| 2129818 | 12/1972 | Fed. Rep. of Germany | 433/37 |
| 3504786 | 10/1985 | Fed. Rep. of Germany | 433/37 |

Primary Examiner—Gene Mancene
Assistant Examiner—Michael Lynch
Attorney, Agent, or Firm—Gary L. Griswold; Walter N. Kirn; James D. Christoff

[57] ABSTRACT

A dental impression tray has an outwardly extending flange that is connected to posterior portions of a trough or channel for receiving a quantity of impression materials. The flange permits the tray to be firmly gripped on the sides of the channel in areas adjacent opposite posterior regions of the patient's dental arch, so that the cured impression material may be disengaged from the arch without excessive permanent distortion of the impression. Preferably, the flange extends along the entire perimeter of the channel and adjacent an occlusal portion of the channel.

4 Claims, 1 Drawing Sheet

DENTAL IMPRESSION TRAY WITH FLANGE

BACKGROUND OF THE INVENTION

1. Field of the Invention

This invention relates to a thermoplastic dental impression tray that may be shaped to conform to a patient's dental arch.

2. Description of the Related Art

Dental impression trays are used to hold impression material for making a model of a patient's oral cavity so that a crown, bridge, denture, restoration or the like can be made. To make the model, a quantity of impression material is placed in an open trough or channel of the tray, and the tray is then pressed onto the dental arch to make a female cast of the desired area of interest. The cured impression is then used to form a male model which replicates the selected area of the patient's arch.

The accuracy of fit of a restoration is due, in large part, on the dimensional accuracy of the impression that is taken from the patient's arch. Consequently, it is important that the impression is not distorted when the tray is removed from the mouth.

Recently, there has been increased interest in the use of thermoplastic impression trays which may be heated and then shaped to closely conform to the patient's dental anatomy. Since dimensions of the dental arch may vary widely from patient to patient, such trays may be molded when heated to adjust the height and width of the channel of the tray to accommodate the selected area of the patient's arch. In this manner, the tray may be shaped to conform to the arch so that an accurate impression may be made, while enabling the relatively expensive impression material to fully surround the selected area of the arch without wastage. Examples of such moldable impression trays are described in U.S. Pat. Nos. 4,227,877, 4,361,528 and 4,657,509.

Often, a considerable force must be used to disengage the cured impression material from the arch. The impression material closely conforms to the arch and a vacuum may be formed between the impression material and the arch as the tray is pulled, rendering disengagement difficult. In addition, the teeth and adjacent recesses often form undercuts in the impression material, such that the impression must be spread apart during disengagement of the impression from the arch.

Typically, the dentist will separate posterior portions of the cured impression from the arch before separating anterior portions of the impression. The channel of the tray normally has an open posterior end, and it is thus easier to release the vacuum formed between the impression material and the arch in areas adjacent the open end of the channel. Once the vacuum is released, it is somewhat easier to pull remaining portions of the impression including anterior portions from corresponding regions of the arch.

Conventionally, dentists purchase flat sheets of thermoplastic material and form the sheets in their offices to the shape of an impression tray. In some cases, handles are molded to the front of the tray to aid in delivery of the tray with the impression material to the oral cavity. The handle also enables the dentist to exert leverage to release posterior regions of the tray from the arch. However, such handles hinder shaping of the thermoplastic material when softened in anterior regions of the tray where the latter is joined to the handle.

Thermoplastic impression trays without handles are normally removed from the arch by placing the fingers over a buccal-gingival edge of the channel in posterior regions of the tray, and exerting a force in an occlusal direction to release posterior portions of the impression from corresponding posterior regions of the arch. However, such practice may spread apart the walls of the channel and permanently distort the impression since considerable force must often be used to release the vacuum. In addition, uncured impression material often is forced over the gingival edges of the channel as the tray is placed onto the arch, thus increasing the difficulty of gripping the buccal-gingival edge of the channel with the fingers after the impression material has cured.

SUMMARY OF THE INVENTION

The present invention concerns a dental impression tray comprised of thermoplastic material and having an elongated channel adapted to receive a quantity of impression material. The channel has a posterior portion and is of a size sufficient to extend about at least a portion of a dental arch. The tray includes a flange connected to the posterior portion of the channel, and the flange extends outwardly from the channel for facilitating removal of the tray from the mouth. The tray is devoid of any handle greater than about 15 milimeters in overall length measured in a direction away from the channel.

The flange functions to distribute forces along the length of the channel as the dentist's fingers engage the flange to pull the tray away from the arch. As such, there is less tendency for sides of the channel and the impression therein to be permanently distorted as the cured impression is pulled away from the arch. The thermoplastic tray is also relatively comfortable for the patient, since the tray when warmed can be shaped to conform to the arch and, as a result, the posterior flanges do not excessively intrude into the area of the patient's cheeks.

DETAILED DESCRIPTION OF THE PREFERRED EMBODIMENT

Figure 1:
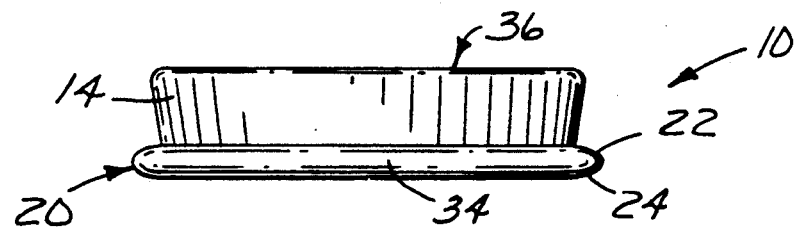
FIG. 1 is a front elevational view of a dental tray constructed in accordance with the present invention.
Figure 2:
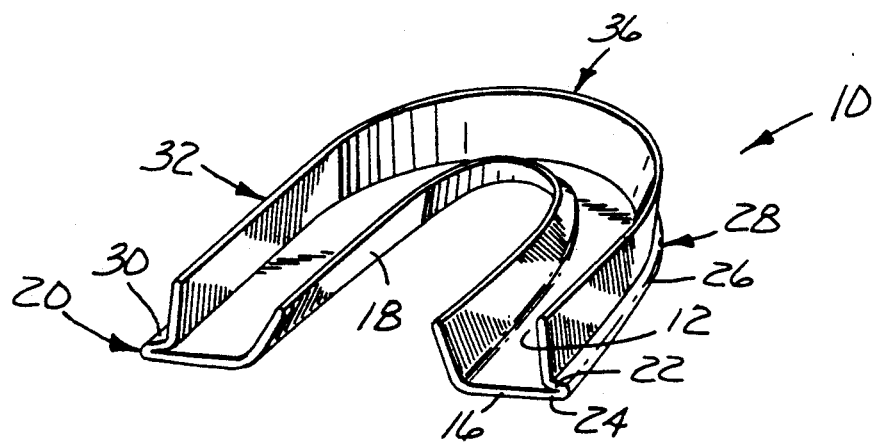
FIG. 2 is a rear, top and left side perspective view of the tray shown in FIG. 1.
Figure 3:
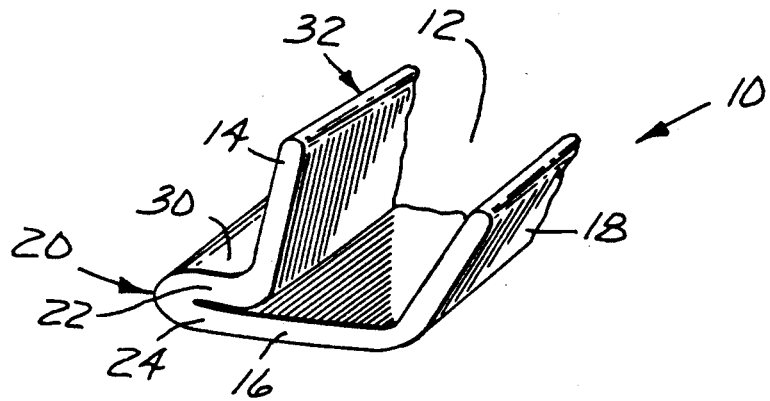
FIG. 3 is an enlarged rear, top and left side perspective view in fragmentary form of a right posterior portion of the tray shown in FIGS. 1 and 2.

A dental tray 10 in accordance with the present invention is shown in FIGS. 1-3 and is made from a single sheet of thermoplastic material. The tray 10 has an overall, generally U-shaped configuration in plan or bottom view.

Preferred thermoplastic molding compositions for making the tray 10 are described in our copending U.S. patent applications Ser. Nos. 07/484,695 and 07/484,692, the disclosures of which are incorporated in this specification by reference. Such compositions comprise a blend which includes polycaprolactone, and are characterized as being solid at 38° C., and having a melting or softening point that can comfortably be withstood by oral tissues. The heated tray 10 may thus be shaped while in the oral cavity or, if desired, while outside of the oral cavity.

The tray 10 includes an elongated, continuous channel 12 having an open top. The channel 12 includes a buccal side 14, an occlusal side 16 and a lingual side 18 adapted to extend about buccal, occlusal and lingual regions respectively of a dental arch. As used herein, "dental arch" means the dentulous or edentulous maxillary or mandibular alveolar ridge (i.e., the bony ridge of either jaw and the surrounding mucosae along with any associated teeth), and does not include the palatal area of the oral cavity.

The channel 12 includes a folded section or flange 20 having a gingival portion 22 that is integrally connected to the occlusal-most end of the buccal side 14, and an occlusal portion 24 that is integrally coupled to a buccal-most end of the occlusal side 16. Typically, the tray 10 is shipped to the dentist in a configuration such that the gingival portion 22 extends essentially parallel to the occlusal portion 24 and is in flat, face-to-face contact with the latter. In this configuration, the buccal side 14 extends at an angle of about 90 degrees relative to the gingival portion 22, and the occlusal side 16 is coplanar with the occlusal portion 24. The lingual side 18 curves upwardly and outwardly away from the occlusal side 16 and has an outer straight section which lies at an angle of about 120 degrees relative to the occlusal side 16.

Preferably, the overall length of the flange 20 measured from the adjacent buccal surface of the buccal side 14 in a direction transverse to the longitudinal axis of the channel 12 is in the range of about 2 millimeters to about 15 millimeters, and more preferably is in the range of about 3 millimeters to about 10 millimeters. Additionally, the flange 20 includes three integrally interconnected sections: a first flange section 26 located in a left posterior portion 28 (FIG. 2) of the tray 10, a second flange section 30 located in a right posterior portion 32 opposed from said left posterior portion 28, and a third flange section 34 (FIG. 1) located in an anterior portion 36 of the tray 10.

Once the tray 10 is heated to its softening temperature, the tray 10 is pliable and may be molded by hand to closely conform to the dental arch. If, for example, a relatively wide channel is needed to accommodate the arch, the tray 10 when softened may be formed so that the flange 20 is partially unfolded and moves from the orientation shown in FIG. 1-3 to an orientation wherein the portions 24, 26 are pivoted away from each other. The movement of the gingival portion 22 away from the occlusal portion 24 enables the previously gathered portion of the channel 12, namely the flange 20, to be molded along with the sides 14, 16 and 18 to permit the occlusal dimension or height of the channel 12 to be enlarged as necessary. In practice, either or both of the sides 14, 18 may be extended in height by proper handforming of the softened channel 12. In addition to enlarging the height of the channel 12, or as an alternative to the latter, it is also possible to enlarge the buccal-lingual width of the channel 12 once the flange 20 is unfolded or partially unfolded.

Advantageously, the flange 20 extends along the entire lower perimeter of the channel 12 including anterior as well as both posterior portions of the tray 10. As such, the flange 20, whether in the configuration shown in FIG. 1 or FIG. 2, provides convenient structure for gripping the tray 10 after the impression of the patient's arch has been taken. The outwardly extending flange 20 enables the dentist's fingers to engage both posterior portions of the tray 10 and release any vacuum formed between the cured impression material and the teeth in areas adjacent the open posterior ends of the channel 12. The tray 10 can thus readily be removed without undue tilting or rotation of the tray and without excessive spreading apart of the sides 14, 18 which might otherwise cause unsatisfactory distortion in the resultant impression.

Further, the tray 10 is devoid of any handle greater than about 15 millimeters in overall length measured from the exterior surface of the buccal side 14 in a direction perpendicular to the longitudinal axis of the channel 12. The flange 20 obviates the need for the relatively long anterior handle typically found in dental impression trays known in the past. Such handles hinder shaping of the malleable material in the anterior region of the arch.

We claim:

1. A dental impression tray having an overall, generally U-shaped configuration in plan view, said tray having an elongated channel adapted to receive a quantity of impression material, said channel having a buccal side, an occlusal side and a lingual side, said tray including a flange extending substantially along the entire length of said channel, said buccal side, said occlusal side, said lingual side and said flange each comprised of a thermoplastic material that is solid at 38° C. and that has a melting or softening temperature that can comfortably be withstood by oral tissues, said channel including opposed posterior portions and being of a size sufficient to extend about at least a portion of a dental arch, said flange including a first flange section connected on one of said posterior portions, and a second flange section connected to the other of said posterior portions, each of said flange sections extending outwardly in opposite directions from said channel for facilitating removal of said tray from the mouth.

2. The tray according to claim 1, wherein said flange extends in a direction substantially parallel to said occlusal side.

3. The tray according to claim 1, wherein said flange is directly connected to said occlusal side of said channel.

4. The tray according to claim 1, wherein said flange extends continuously substantially along the length of said channel.

* * * * *

UNITED STATES PATENT AND TRADEMARK OFFICE
CERTIFICATE OF CORRECTION

PATENT NO. : 5,026,278

DATED : June 25, 1991

INVENTOR(S) : Joel D. Oxman and F. Andrew Ubel III

It is certified that error appears in the above-identified patent and that said Letters Patent is hereby corrected as shown below:

Col. 4, line 43, "on" should be -- to --.

Signed and Sealed this

Sixteenth Day of March, 1993

Attest:

STEPHEN G. KUNIN

Attesting Officer

Acting Commissioner of Patents and Trademarks